(12) United States Patent
Giampapa et al.

(10) Patent No.: US 10,098,922 B1
(45) Date of Patent: Oct. 16, 2018

(54) INCREASING TELOMERE LENGTH IN A CELL

(71) Applicant: OPTIGENEX, INC., Melissa, TX (US)

(72) Inventors: Vincent C Giampapa, Montclair, NJ (US); Linda Crouse, Ben Lemond, CA (US)

(73) Assignee: Optigenex, Inc.

( * ) Notice: Subject to any disclaimer, the term of this patent is extended or adjusted under 35 U.S.C. 154(b) by 0 days.

(21) Appl. No.: 15/827,223

(22) Filed: Nov. 30, 2017

(51) Int. Cl.
*A61K 36/74* (2006.01)
*A61K 9/70* (2006.01)

(52) U.S. Cl.
CPC .......... *A61K 36/74* (2013.01); *A61K 9/7023* (2013.01)

(58) Field of Classification Search
CPC combination set(s) only.
See application file for complete search history.

(56) References Cited

U.S. PATENT DOCUMENTS

| | | | |
|---|---|---|---|
| 5,489,508 A | 2/1996 | West et al. | |
| 5,656,665 A | 8/1997 | Yu et al. | |
| 5,741,677 A | 4/1998 | Kozlowski et al. | |
| 6,039,949 A * | 3/2000 | Pero | A61K 36/74 424/769 |
| 6,964,784 B2 * | 11/2005 | Pero | A61K 36/74 424/725 |
| 7,846,904 B2 | 12/2010 | Harley et al. | |
| 7,955,626 B2 | 6/2011 | Pero | |
| 8,372,448 B2 * | 2/2013 | Pero | A61K 36/74 424/725 |
| 8,372,449 B2 * | 2/2013 | Pero | A61K 36/74 424/725 |
| 8,968,801 B1 * | 3/2015 | Giampapa | A61K 36/74 424/725 |
| 8,974,839 B2 | 3/2015 | Giampapa | |
| 9,345,733 B1 * | 5/2016 | Giampapa | A61K 36/28 |
| 2009/0263367 A1 * | 10/2009 | Foley | A61K 31/352 424/94.4 |
| 2014/0079836 A1 * | 3/2014 | McDaniel | A61K 31/05 424/777 |
| 2014/0308248 A1 * | 10/2014 | Giampapa | A61K 36/00 424/93.3 |
| 2015/0338387 A1 * | 11/2015 | Ehrenkranz | A61B 5/6898 424/450 |
| 2017/0128355 A1 | 5/2017 | Giampapa et al. | |

OTHER PUBLICATIONS

Mammone T. et al. A Water Soluble Extract from Uncaria tomentosa is a Potent Enhancer of DNA Repair . . . Phytotherapy Research 20(3)178-183, Mar. 2006. (Year: 2006).*

Na, M. et al. Cytoprotective Effect on Oxidative Stress and Inhibitory Effect on Cellular Aging of Uncaria sinensis Havil. J of Ethnopharmacology 95(2-3)127-132, Dec. 2004. (Year: 2004).*

Aviv et al. (2011) Impartial comparative analysis of measurement of leukocyte telomere length/DNA content by Southern blots and qPCR. Nucleic Acids Research 39(20): e134.

Bodnar et al. (1998) Extension of life-span by introduction of telomerase into normal human cells. Science 279: 349-352.

Cawthon, RM (2002) Telomere measurement by quantitative PCR. Nucleic Acids Research 30(10): e47.

Greider, CW (1990) Telomeres, telomerase and senescence. BioEssays 12(8): 363-369.

Harley et al. (1990) Telomeres shorten during ageing of human fibroblasts. Nature 345(6274): 458-460.

Hasnisa et al. (2017) In vivo toxicity studies of a mixture of *Hibiscus sabdariffa* L., *Clinacanthus nutans* L., and *Stevia* leaves in Sprague Dawley rats. J. Trop. Agric. and Fd. Sci. 45(1): 111-119.

Joeng et al. (2004) Long lifespan in worms with long telomeric DNA. Nature Genetics 36(6): 607-611.

Lamm et al. (2001) Persistent response to pneumococcal vaccine in individuals supplemented with a novel water soluble extract of Uncaria tomentosa, C-Med-100® Phytomedicine 8(4): 267-274.

O'Callaghan and Fenech (2011) A quantitative PCR method for measuring absolute telomere length. Biological Procedures Online 13: 3 (pp. 1-10).

Parasuraman, S. (2011) Toxicological screening. Journal of Pharmacology and Pharmacotherapeutics 2(2): 74-79.

Sheng et al. (2000) Enhanced DNA repair, immune function and reduced toxicity of C-MED-100™, a novel aqueous extract from Uncaria tomentosa. J. Ethnopharmacology 69: 115-126.

Sheng et al. (2001) DNA repair enhancement of aqueous extracts of Uncaria tomentosa in a human volunteer study. Phytomedicine 8(4): 275-282.

Zhang et al. (2017) Oral acute and chronic toxicity of beta, beta-dimethylacrylalkannin in mice and rats. Fundamental Toxicological Sciences 4(2): 45-56.

Ciccia et al. (2010) The DNA damage response: Making it safe to play with knives. Molecular Cell 40: 179-204.

Roake et al. (2016) Telomere-lengthening mechanism revealed. Nature 539: 35-35.

* cited by examiner

Primary Examiner — Ralph J Gitomer
(74) Attorney, Agent, or Firm — H. Jay Spiegel

(57) ABSTRACT

A method of increasing the lengths of telomeres in animal cells is practiced by administering an aqueous extract of an *Uncaria* species to an animal. The animal may be a human and the *Uncaria* species may be *Uncaria tomentosa*. Human subjects receiving a daily dose of an aqueous extract of *Uncaria tomentosa* for a sufficient period of time exhibited an increase in telomere length relative to a baseline measurement taken prior to treatment. The extract may be administered topically or systemically.

20 Claims, 11 Drawing Sheets even though the QA was not isolated and purified from the Uncaria water extract, suggesting that the purification of QA or QAS is not needed to produce a suitable bioactive agent. The referenced invention is not directed to the administration of an Uncaria water extract, nor is it directed to a method of lengthening telomeres.

US 10,098,922 B1

INCREASING TELOMERE LENGTH IN A CELL

BACKGROUND OF THE INVENTION

The present invention relates to a method of increasing the length of a telomere in an animal cell. The invention is practiced by administering an aqueous extract of an *Uncaria* species to an animal.

A telomere is a region of repetitive DNA sequence at the end of a chromosome, which protects the end of the chromosome from truncation and from fusion with a neighboring chromosome. Accordingly, telomeres provide stability to linear DNA molecules (Greider, C W (1990) BioEssays 12(8):363-369). The telomeric TTAGGG repeat sequences capping the ends of chromosomes have been shown to shorten during replicative ageing of normal cells (Harley et al. (1990) Nature 345(6274): 458-460).

Telomeres are consumed during cell division, but are replenished by the action of the enzyme telomerase reverse transcriptase. Human somatic cells without telomerase gradually lose telomeric sequences as a result of incomplete replication. Various methods for increasing the length of a telomere in a cell are known in the art (Joeng et al. (2004) Long lifespan in worms with long telomeric DNA. Nature Genetics 36(6): 607-611; Bodnar et al. (1998) Extension of life-span by introduction of telomerase into normal human cells. Science 279(5349): 349-352). These methods primarily rely on increasing the activity of telomerase. For example, a study that looked at normal human cells over-expressing the human telomerase catalytic subunit demonstrated elongated telomeres as a result of enhanced telomerase activity (Bodnar et al., supra) As distinguished from the present invention, these prior art methods do not provide a means of enhancing DNA repair in combination with a method of increasing the activity of telomerase, or otherwise increasing telomere length.

Methods for measuring telomere length are well known in the art and are described, for example, in Cawthon, R M (2002) Nucleic Acids Res. 30(10): e47, Harley et al. (1990) Nature 345: 458-460, O'Callaghan and Fenech (2011) Biological Procedures Online 13:3, U.S. Pat. No. 5,489,508 (West et al., issued Feb. 6, 1996), and U.S. Pat. No. 5,741,677 (Kozlowski et al., issued Apr. 21, 1998). Any method of measuring telomere length can be used in the present invention.

Any nucleated cell type may be used for the purpose of measuring telomere length. Lymphocytes and buccal cells are commonly used, as they are easily obtained from patients (O'Callaghan and Fenech (2011) Biological Procedures Online 13:3). Peripheral leukocytes are also commonly used for telomere length assessment (Aviv et al. (2011) Nucleic Acids Research 39(20): e134). As described herein, the terms "peripheral leukocytes" and "white blood cells" are used interchangeably. Genomic DNA isolated from the nucleated cell type of interest is used to measure telomere length. Methods for isolating genomic DNA are well known in the art.

AC-11°, formerly known as C-Med 100, is a hot water extract of the bark of the plant *Uncaria tomentosa*. Its characterization and method of preparation are described in U.S. Pat. No. 6,039,949 to Pero (issued Mar. 21, 2000). Animal and human studies have demonstrated a beneficial effect of AC-11® on enhancing DNA repair and immune function (Sheng et al. (2000) J. Ethnopharmacol. 69: 115-126; Sheng et al. (2001) Phytomedicine 8(4): 275-282).

U.S. Pat. No. 6,039,949 to Pero discloses a water soluble extract of an *Uncaria* species, as well as a method for preparing it. The reference further discloses oral administration of the extract to rats. The reference does not, however, contemplate a method of lengthening the telomeres or otherwise manipulating or maintaining telomere length. Likewise, the reference does not contemplate measuring telomere length.

Sheng et al. (2001, supra) disclose oral administration of C-MED-100 (a water extract of *Uncaria tomentosa*) to twelve healthy adult human volunteers. The doses tested were daily doses of 250 mg and 350 mg, for 8 weeks. A decrease of DNA damage and an increase in DNA repair was seen in both supplement groups when compared to an untreated control group. The reference does not disclose a method of lengthening telomeres and does not contemplate measuring telomere length before and after administration of the supplement.

Lamm et al. (2001, Phytomedicine 8(4):267-274) disclose oral administration of C-MED-100® at a dose of 350 mg×2 times daily for two months, to human volunteers. Study participants supplemented with C-MED-100® were tested for their ability to respond to a 23 valent pneumococcal vaccine as compared to an untreated control group. Statistically significant immune enhancement was observed for those in the supplemented group. The reference does not disclose a method of lengthening telomeres and does not contemplate measuring telomere length before and after administration of the supplement.

U.S. Pat. No. 7,955,626 to Pero (issued Jun. 7, 2011) discloses non-topical administration of a purified quinic acid alkyl ester or a carboxy alkyl ester. The reference discloses a water extract of *Uncaria tomentosa*, as well as further purification of the extract by thin layer chromatography to obtain carboxy alkyl esters (CAE). The invention is not directed to administration of a composition comprising quinic acid. Moreover, the method of the invention does not require the inclusion of quinic acid (in the free acid form or a salt thereof) because the invention is specifically directed to administering a pharmaceutical composition comprising an effective amount of an ester, either a quinic acid alkyl ester or a carboxy alkyl ester, meeting specified criteria. Furthermore, the reference does not disclose measuring telomere length and does not contemplate increasing the length of the telomeres.

U.S. Pat. No. 8,372,449 (Pero, Ronald W., issued Feb. 12, 2013) describes a method of non-topical administration of a pharmaceutical composition comprising a purified and isolated compound selected from the group consisting of quinic acid and a quinic acid salt. The invention is directed to a method for enhancing the response to tumor formation and/or growth in a mammal in need thereof. The pharmaceutical composition is administered in an amount effective to inhibit TNF-α production or to induce apoptosis of white blood cells, where said quinic acid and said quinic acid salt may form an ammonium salt and/or chelate thereof having a bioassay efficacy using $IC_{50}$ in HL-60 cells of approximately 500 μg/ml or less. The disclosure indicates that the bioactive agent of C-MED-100® (a water extract of *Uncaria tomentosa*) in vivo is not quinic acid lactone, but rather is quinic acid and its salts, including its ammonium salt. The in vivo working examples pertain to oral dosing studies in mice and rats, with administration by gavage in rats and via the drinking water in mice. Treatment of mice with C-MED-100® resulted in an increased number of spleen cells, due to the prolongation of lymphocyte half life. In rats, quinic acid (QA) and its ammonium salt (QAA) were about as effective as C-MED-100® at reversing doxorubicin-induced leukopenia. The reference reveals that daily oral doses of C-MED-100® between 250-700 mg have proven efficacious in humans with regard to enhancing anti-inflammatory, DNA repair, immune stimulation, and anti-tumor processes. This reference does not contemplate a method of lengthening the telomeres or otherwise manipulating or maintaining telomere length. Likewise, the reference does not contemplate measuring telomere length before or after administration of quinic acid, a quinic acid salt, or C-MED-100®.

The bioactive component in AC-11®, formerly known as C-MED-100®, is reported to be quinic acid lactone (U.S. Pat. No. 6,964,784, issued Nov. 15, 2005). Moreover, the bioactive agent in vitro is quinic acid lactone (U.S. Pat. No. 8,372,448, issued Feb. 12, 2013), while the in vivo bioactive agent is quinic acid (U.S. Pat. No. 8,372,449, issued Feb. 12, 2013).

U.S. Pat. No. 8,974,839 to Giampapa (issued Oct. 16, 2014) discloses a multi-component supplement composition comprising a water extract of *Uncaria tomentosa*, which is disclosed as being a DNA repair complex. The supplement of the invention also comprises a telomere maintenance complex. However, the water extract of *Uncaria tomentosa* is not disclosed as being a telomere maintenance complex. The reference does not contemplate a method of lengthening the telomeres or otherwise manipulating telomere length. Likewise, the reference does not contemplate measuring telomere length.

U.S. Patent Application No. 2017/0128355 to Giampapa et al. (published May 11, 2017) discloses a method of topically applying a multi-component composition comprising a water soluble extract of an *Uncaria* species. The reference does not contemplate a method of lengthening the telomeres or otherwise manipulating or maintaining telomere length. Likewise, the reference does not contemplate measuring telomere length.

U.S. Pat. No. 5,656,665 to Yu et al. (issued Aug. 12, 1997) discloses a method for visibly reducing a skin wrinkle and for reversing the effect of aging on human facial skin by topically applying to the wrinkle and/or affected facial skin quinic acid or quinolactone. A wide variety of preparations are contemplated. The working examples are directed to testing the various compositions in 90 human volunteer subjects, by topical application to the skin. This reference does not contemplate a method of lengthening the telomeres or otherwise manipulating or maintaining telomere length. Likewise, the reference does not contemplate measuring telomere length before or after administration of quinic acid or quinolactone. The reference does not disclose administering a water extract of *Uncaria tomentosa* to a subject or a cell. Moreover, there is no mention of an extract of *Uncaria tomentosa*. The reference is limited to topical application and does not contemplate other modes of administration.

U.S. Patent Application Publication No. 2015/0338387 to Ehrenkranz (published Nov. 26, 2015) discloses a method for monitoring and adjusting a biometric, such as aging. The method of the invention comprises administering to a subject a supplement selected to effect the state of the selected biometric. The supplement may be formulated for oral administration. Among a long list of possibilities, the supplement may be an extract of *Uncaria tomentosa* and the biometric analyte, among a long list of possibilities, may be telomere length. The reference does not include any working examples, nor does it specifically mention using an extract of *Uncaria tomentosa* to increase the length of a telomere in a cell by administration of the extract to a mammal. Moreover, the reference does not specifically disclose a water extract of *Uncaria tomentosa*.

U.S. Patent Application No. 2014/0079836 to McDaniel (published Mar. 20, 2014) discloses a method for modulating the activity of the gene maintenance process in order to influence the length and/or structural integrity of the telomere in living cells. Quinic acid is disclosed as an exemplary lifespan altering compound. The method of the invention is specifically directed to contacting a cell, tissue, organ, or organism with quinic acid, or an analog or derivative thereof. Quinic acid is disclosed as being naturally found in the coffee cherry. The disclosure contemplates lengthening telomeres, as well as modulating the activity or level of at least one of the telomere length maintenance genes or modulating the activity or level of telomerase. This reference does not contemplate using a water extract of *Uncaria tomentosa* for any purpose. There is no mention of an *Uncaria* species. The reference does not specifically point to quinic acid as modulating the length of the telomere in living cells. There are no working examples pertaining to quinic acid or telomere lengthening in an organism. Working examples directed to telomere length maintenance are provided, but these are in vitro experiments (cells in culture) examining the effects of green tea extract, coffee cherry extract, and idebenone.

It has now been shown by Applicants that administration of an aqueous extract of an *Uncaria* plant to a subject results in telomere lengthening.

SUMMARY OF THE INVENTION

The present invention relates to a method of increasing the length of a telomere in an animal cell. The invention is practiced by administering an aqueous extract of an *Uncaria* species to an animal in an amount and for a period of time sufficient to increase the length of said telomere, and measuring the length of said telomere before and after administration of said extract. In a preferred embodiment, the method of the invention is directed to increasing the length of a telomere in a mammalian cell, said method comprising administering an aqueous extract of an *Uncaria* species to a mammal, or a mammal in need thereof, in an amount and for a period of time sufficient to increase the length of said telomere, and measuring the length of said telomere before and after administration of said extract.

As such, it is a first object of the present invention to provide a method of increasing telomere length in a cell, said method comprising administering to a subject an aqueous extract of an *Uncaria* species in an amount and for a period of time sufficient to increase the length of a telomere in a cell of said subject.

It is a further object of the present invention to provide a method of increasing telomere length in a cell, said method comprising orally administering to a subject a daily dose of about 200 mg to about 700 mg of an aqueous extract of an *Uncaria* species for a period of time sufficient to increase the length of a telomere in a cell of said subject.

It is a still further object of the present invention to provide a method of increasing telomere length in a cell, said method comprising administering to a subject an aqueous extract of an *Uncaria* species in a pharmaceutically effective amount and for a period of time sufficient to increase the length of a telomere in a cell of said subject, wherein said *Uncaria* species is *Uncaria tomentosa*.

It is a still further object of the present invention to provide a method of increasing telomere length in a cell, said method comprising orally administering to a subject a daily dose of about 200 mg to about 700 mg of an aqueous extract of an *Uncaria* species for a period of time sufficient to increase the length of a telomere in a cell of said subject, wherein said *Uncaria* species is *Uncaria tomentosa*, wherein the period of time sufficient to increase the length of a telomere in a cell of said subject is at least one year, and further wherein said aqueous extract comprises a minimum of 8% carboxy alkyl esters (CAEs) (weight/weight (w/w)).

It is a still further object of the present invention to provide a method of increasing telomere length in a cell, said method comprising orally administering to a subject an aqueous extract of an *Uncaria* species in an amount and for a period of time sufficient to increase the length of a telomere in a cell of said subject, wherein said aqueous extract of an *Uncaria* species is provided as a capsule, tablet, liquid, or gel, and wherein said *Uncaria* species is *Uncaria tomentosa*. The capsule, tablet, liquid, or gel may be provided as a time-release formula or extended-release formula.

It is a still further object of the present invention to provide a method of increasing telomere length in a cell, said method comprising orally administering to a subject a daily dose of about 700 mg of an aqueous extract of an *Uncaria* species for a period of time sufficient to increase the length of a telomere in a cell of said subject, wherein said *Uncaria* species is *Uncaria tomentosa*, and said subject is a human.

These and other objects, aspects and features of the present invention will be better understood from the following detailed description when read in conjunction with the examples described herein.

DETAILED DESCRIPTION OF THE INVENTION

Figure 1:
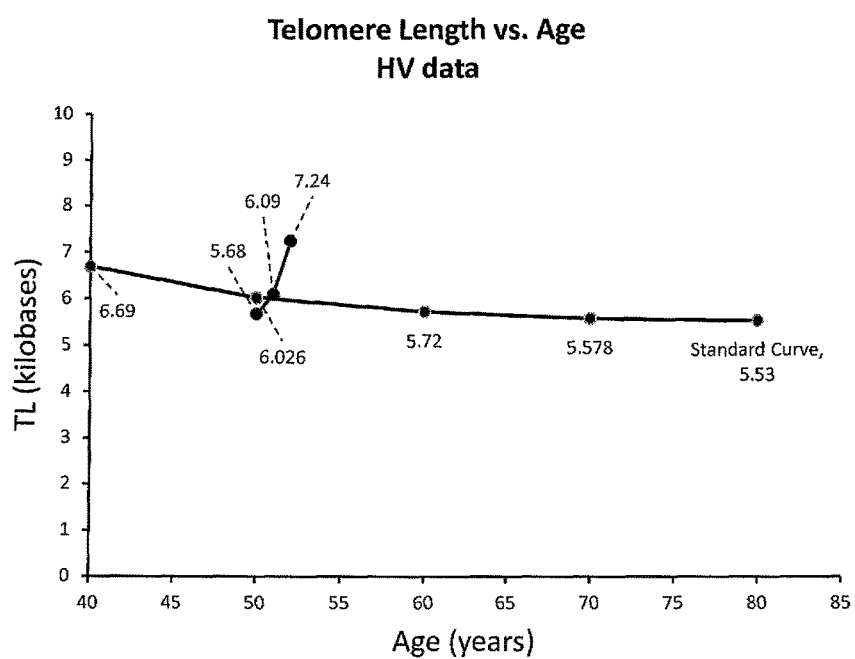
FIG. 1 Telomere length of a human study participant, subject HV, before treatment and after treatment, at timepoints of one year and two years. Treatment was carried out by oral administration of an aqueous extract of *Uncaria tomentosa* formulated into a capsule, at a daily dose of 700 mg. The standard curve provides average telomere lengths for the general population at different ages.
Figure 2:
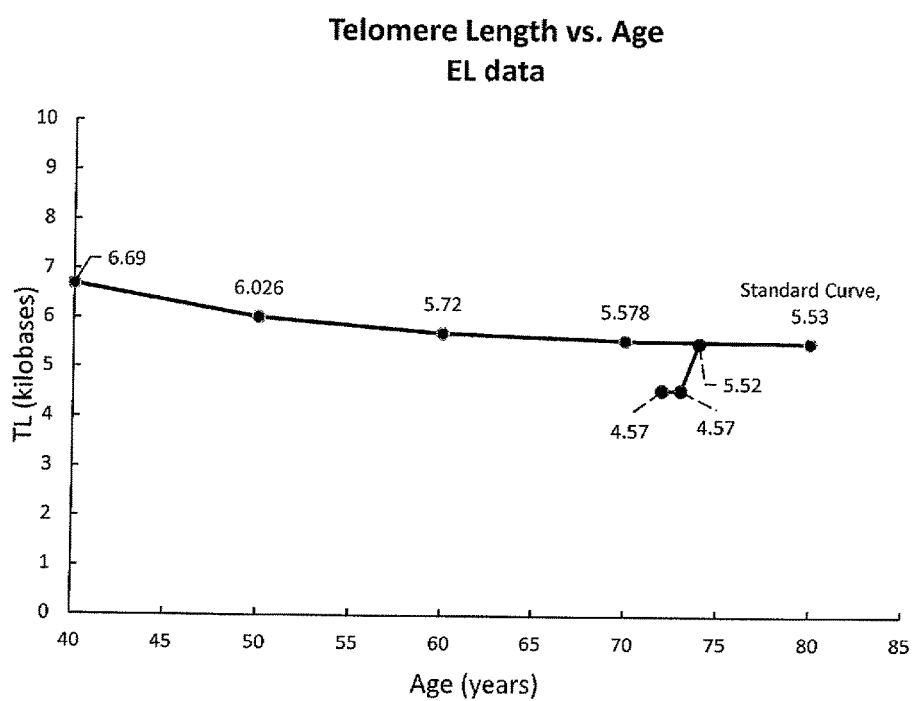
FIG. 2 Telomere length of a human study participant, subject EL, before treatment and after treatment, at timepoints of one year and two years.
Figure 3:
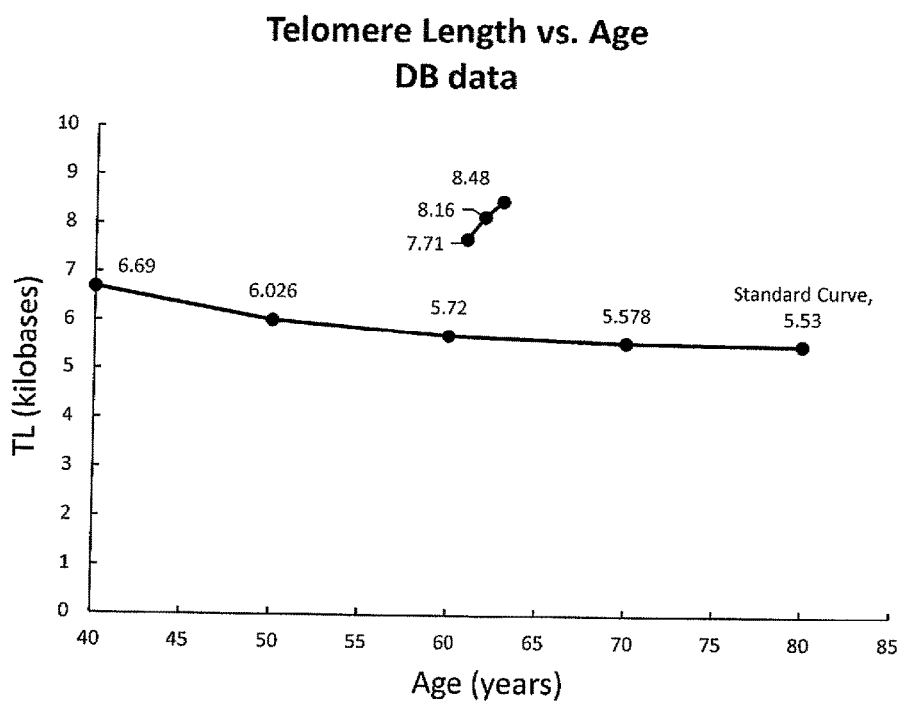
FIG. 3 Telomere length of a human study participant, subject DB, before treatment and after treatment, at timepoints of one year and two years.
Figure 4:
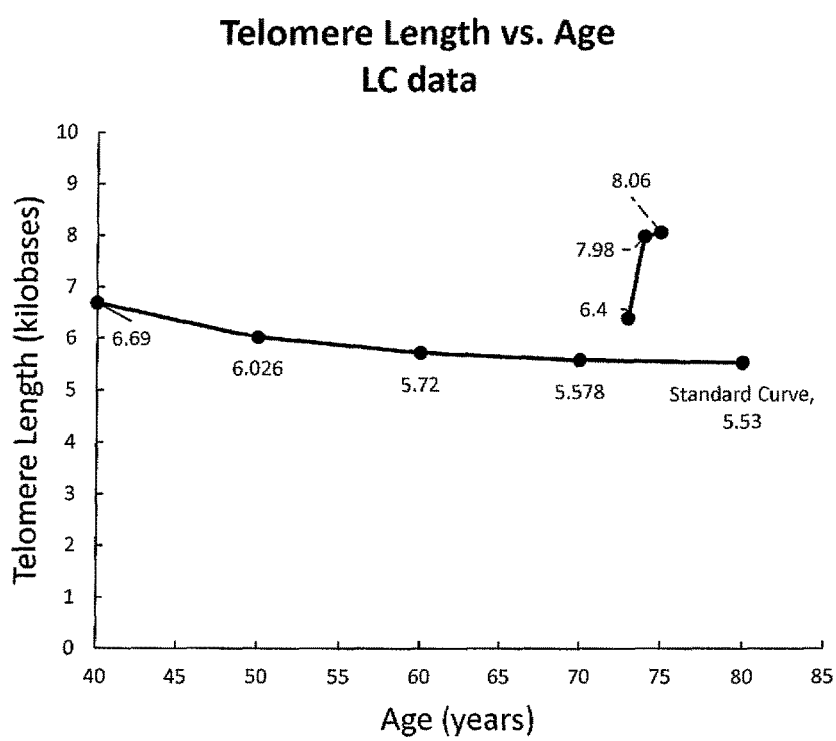
FIG. 4 Telomere length of a human study participant, subject LC, before treatment and after treatment, at timepoints of one year and two years.

Methods for administering a plant extract to an animal, thereby delivering the plant extract to a cell of the animal, are well known in the art. Standard delivery means are contemplated. Accordingly, the plant extract may be formulated into a delivery means such as a capsule, tablet, liquid, gel, lotion, cream, or ointment to facilitate a desired dosing regimen. The plant extract may be administered orally, topically, or via a transdermal patch. The delivery means, particularly a capsule, tablet, liquid, or gel may be provided as a time-release formula or extended-release formula.

Methods for measuring telomere length are well known in the art and are described, for example, in Cawthon, R M (2002, supra), Harley et al. (1990, supra), O'Callaghan and Fenech (2011, supra), U.S. Pat. No. 5,489,508 (West et al., issued Feb. 6, 1996), and U.S. Pat. No. 5,741,677 (Kozlowski et al., issued Apr. 21, 1998), as well as the examples provided herein. The quantitative polymerase chain reaction (qPCR) of Cawthon, R M (2002, supra) is a fluorescence-based assay that uses a primer pair where each primer is designed to allow DNA polymerase to extend from its 3'-end when it is hybridized to telomere hexamer repeats, but not when it is hybridized to the other primer. Any method of measuring telomere length can be used in the method of the present invention.

The aqueous extract of *Uncaria tomentosa* used in the examples set forth herein below has been well characterized in over 20 years of research (see e.g., U.S. Pat. No. 6,039,949 to Pero, R W, issued Mar. 21, 2000 and U.S. Pat. No. 8,372,449 to Pero, R W, issued Feb. 12, 2013). The aqueous extract was spray dried onto a carrier element, such as maltodextrin, to obtain a commercial product comprising a minimum of 8% (w/w) carboxy alkyl esters (CAEs), with the concentration of CAEs ranging from 8-10% (w/w), as described in U.S. Pat. No. 8,372,449 (supra) and Sheng et al. (2001, supra). This product is also known as AC-11®. The examples described herein were carried out using capsules containing 350 mg of AC-11® prepared in this manner.

AC-11® has been subjected to rigorous toxicological studies (Sheng et al. (2000) J. Ethnopharmacology 69: 115-126). No acute toxicity was observed in rats given a series of single oral doses of the product up to a dose of 8 g/kg body weight or human volunteers given a daily dose of 5 mg/kg for six consecutive weeks. Rats treated daily with *U. tomentosa* extracts at the doses of 10-80 mg/kg for 8 weeks or 160 mg/kg for 4 weeks showed no signs of acute of chronic toxicity (Sheng et al., 2000, supra). Furthermore, the bark of the *U. tomentosa* vine is harvested from the wild, specifically the Amazonian rainforest. This is the starting material for the hot water extraction process. No solvents other than water are used in the extraction process. Moreover, AC-11 has an exemplary microbiological profile and an unblemished safety record in over 15 years of commercial use. The toxicological screening assays used to evaluate the safety profile of AC-11 are well known in the art (see e.g., Hasnisa et al. (2017) J. Trop. Agric. and Fd. Sci. 45(1): 111-119; Zhang et al. (2017) Fundam. Toxicol. Sci. 4(2):

45-56; and Parasuraman, S. (2011) J. Pharmacol. and Pharmacotherapeutics 2(2): 74-79).

In a preferred embodiment the animal is a mammal. In a further embodiment, the animal is a rodent, including a mouse or rat. In a further embodiment, the animal is a primate, including a human.

In some embodiments, the subject is a human having a disease or disorder, such as Alzheimer's disease, Parkinson's disease, or cancer. In other embodiments, the subject is a human in apparent good health.

In a preferred embodiment of the method of the invention, the extract is administered orally and the dose is about 700 mg/day. In other embodiments, the dose ranges from about 200 mg/day to about 700 mg/day. In some embodiments, the daily dose is about 350 mg. In other embodiments, the daily dose is about 250 mg. Oral dosing in rats demonstrated an $LD_{50}$>8 g/kg (Sheng et al. (2001) J. Ethnopharm. 69: 115-26). Given the high level of tolerance demonstrated in rats, a dose of 10 g/day administered to a subject is contemplated, up to a dose that falls below the level that would be toxic to the subject. Likewise, while a dose of 200 mg/day is contemplated to be effective to increase the length of a telomere in a cell of a subject, when administered for a sufficient period of time, doses below 200 mg/day are also contemplated when effective to increase the length of a telomere in a cell of the subject, when administered for a sufficient period of time. The doses described herein refer to an extract comprising 8-10% (w/w) CAEs.

In a preferred embodiment, the period of time sufficient to increase the length of telomeres in cells of a subject is a time period of up to one year. In other embodiments, the period of time sufficient to increase the length of telomeres in cells of a subject ranges from about 6 months to about 2 years. In some embodiments, regular dosing, including daily dosing of the *Uncaria* extract, is continued for the life of the subject. The duration of treatment can vary widely and still result in increasing telomere length. One of ordinary skill in the art with this disclosure having been reviewed can determine a pharmaceutically effective dosage to result in telomere lengthening.

In a preferred embodiment, the frequency of dosing is once daily. In other embodiments, the dosing frequency is twice daily. In still other embodiments, the dosing frequency ranges from at least once daily to at least once monthly. The *Uncaria* extract may be administered once daily, twice daily, once every other day, once every third day, once a week, or once a month. In still other embodiments, a transdermal patch is applied once every other day or once a week and delivers the extract to the subject over an extended period of time. Accordingly, the dosing frequency can vary widely and still result in an increase in telomere length.

In a preferred embodiment, the subject's telomeres are measured before administration of the extract and after a period of time sufficient to increase the length of a telomere in a cell of a subject. In other embodiments, samples are taken from a subject before administration of the *Uncaria* extract and at various timepoints during the treatment period. Samples may be preserved and telomere length may be assessed any time after obtaining the sample. In some embodiments, the samples are collected, preserved for a period of time, and then subjected to measurement of telomere length after all samples have been obtained from the subject.

In a preferred embodiment, the *Uncaria* extract is formulated for oral administration, as a capsule, tablet, liquid, syrup, or gel. In other embodiments, the *Uncaria* extract is formulated for topical administration, as a lotion, cream, ointment, or gel. In another embodiment, the *Uncaria* extract is formulated for systemic administration, as a transdermal patch.

In a further preferred embodiment of the method of the invention, the *Uncaria* species is *Uncaria tomentosa*.

EXAMPLES

The examples that follow illustrate aspects of the invention and provide one of ordinary skill in the art with a complete description of how to make and use the present invention, and are not intended to limit the scope of what the inventors regard as their invention nor are they intended to represent that the experiments below are all or the only experiments performed. Rather, these non-limiting examples provide specific methodology useful in practicing the invention.

Example 1

Figure 5:
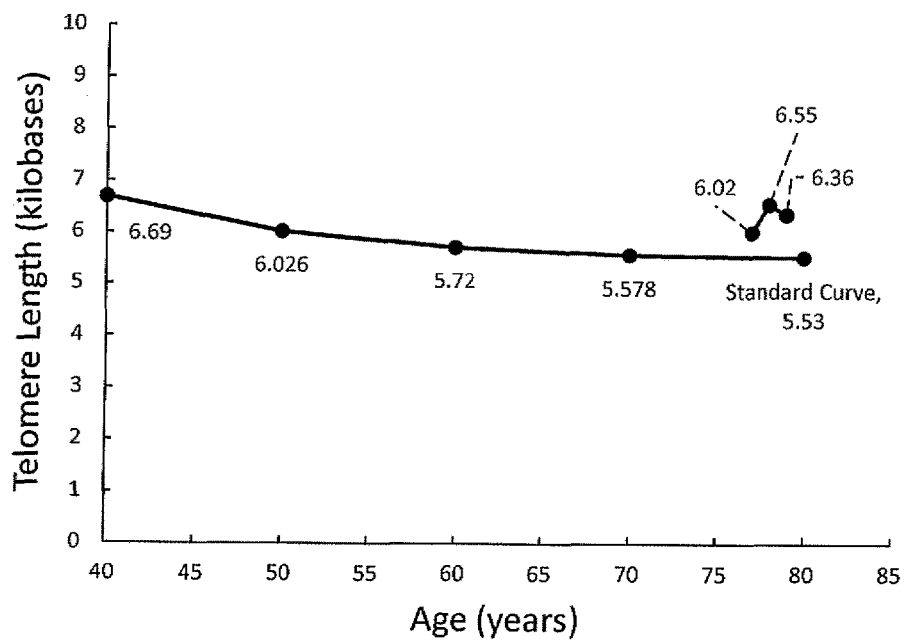
FIG. 5 Telomere length of a human study participant, subject RC, before treatment and after treatment, at timepoints of one year and two years. This subject stopped using AC-11®, for 4 to 5 months, during the second year of the study, in accordance with their doctor's request.
Figure 6:
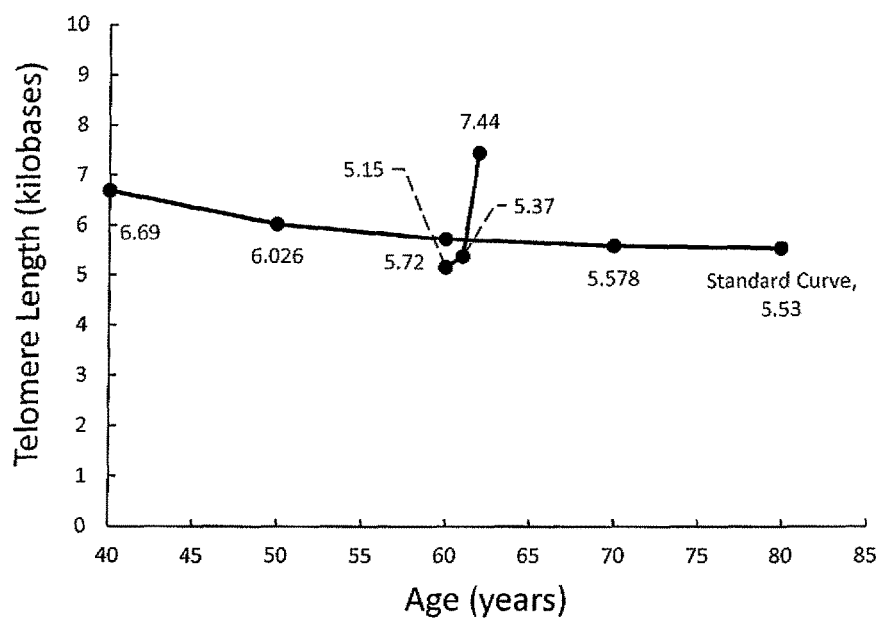
FIG. 6 Telomere length of a human study participant, subject LM, before treatment and after treatment, at timepoints of one year and two years.
Figure 7:
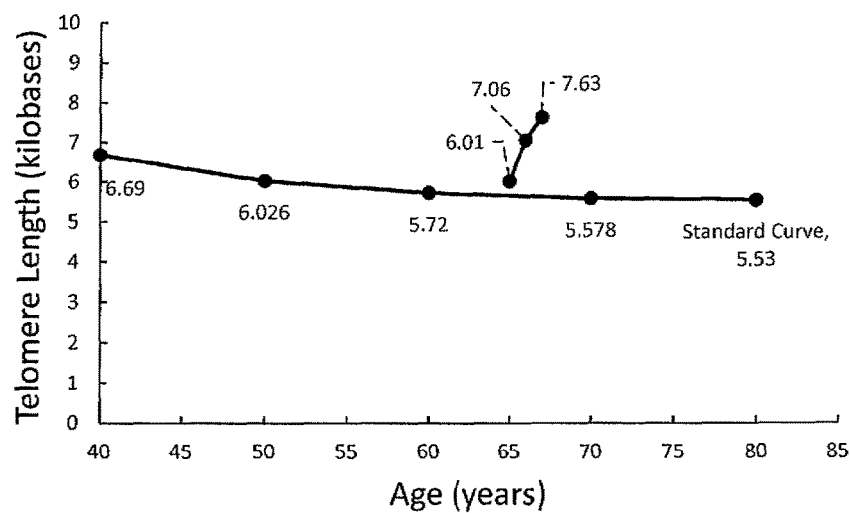
FIG. 7 Telomere length of a human study participant, subject KC, before treatment and after treatment, at timepoints of one year and two years.
Figure 8:
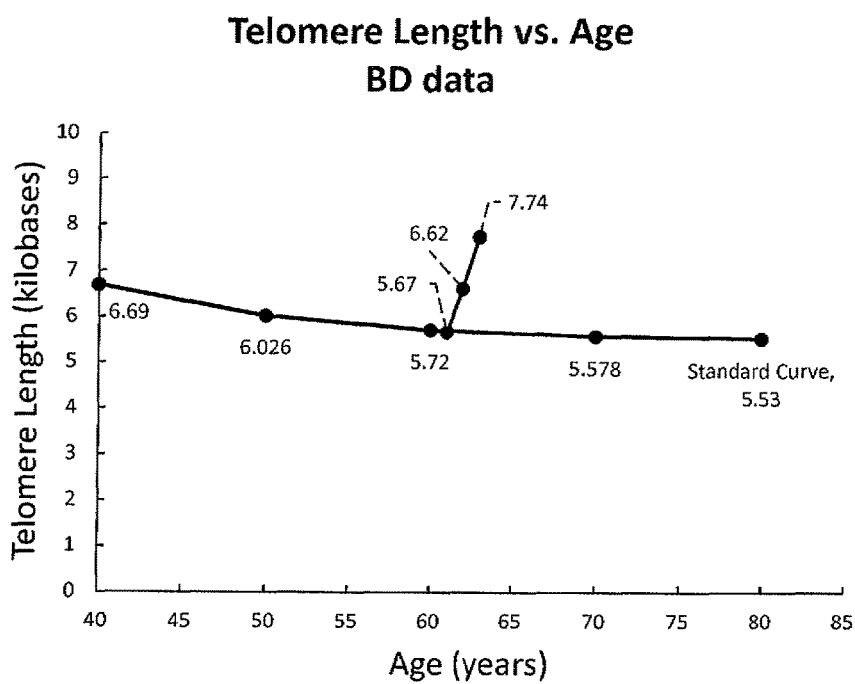
FIG. 8 Telomere length of a human study participant, subject BD, before treatment and after treatment, at timepoints of one year and two years.
Figure 9:
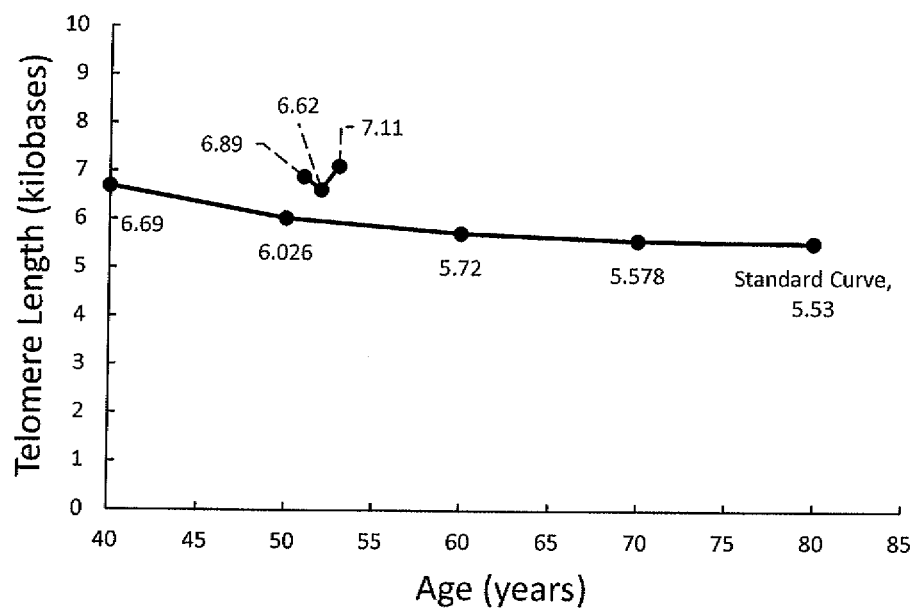
FIG. 9 Telomere length of a human study participant, subject MM, before treatment and after treatment, at timepoints of one year and two years. This subject stopped using AC-11®, for 4 to 5 months, in accordance with their doctor's request.
Figure 10:
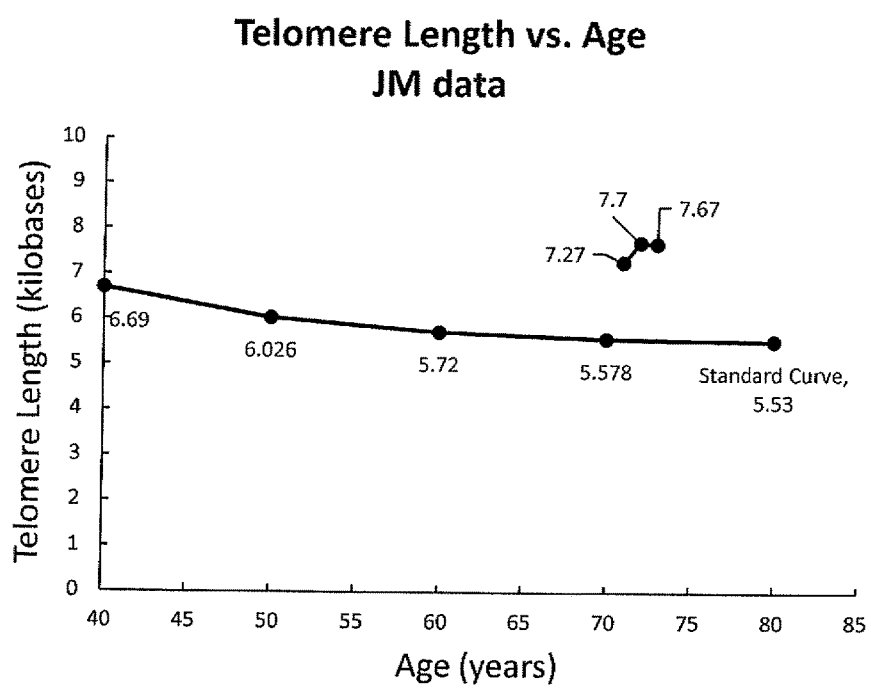
FIG. 10 Telomere length of a human study participant, subject JM, before treatment and after treatment, at timepoints of one year and two years.
Figure 11:
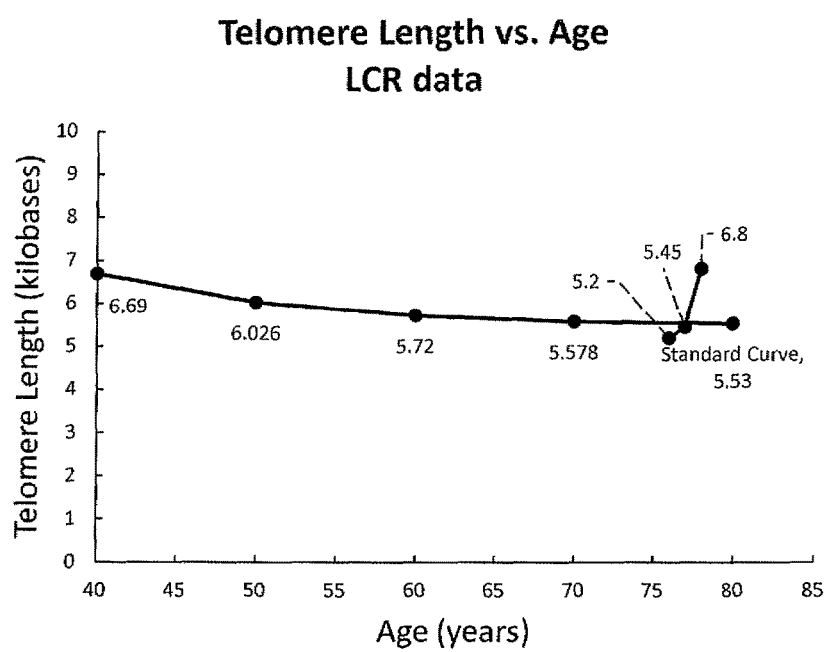
FIG. 11 Telomere length of a human study participant, subject LCR, before treatment and after treatment, at timepoints of one year and two years.

AC 11® Human Pilot Study: The Impact of AC-11® on Telomere Length in an Aging Population The average person's telomeres shorten each year in adulthood. That fact is reflected in the bold line on each of the figures. A pilot study of 11 human volunteers measured telomere lengths before treatment with AC-11® and after treatment, at timepoints of one year and two years. Treatment was carried out by oral administration of an aqueous extract of *Uncaria tomentosa* formulated into a capsule, at a daily dose of 700 mg. The extract comprised 8-10% CAEs (w/w). The telomeres of all 11 subjects increased in length, sometimes dramatically. FIGS. 1-11 provide both the actual telomere length (in kilobases) and the percentile scores of each subject for a clear visual illustration. The results were surprising and unexpected. The only exceptions were two subjects (RC and MM) who stopped using AC-11®, each for 4 to 5 months, in accordance with their doctor's request (FIGS. 5 and 9). Theirs were the only telomeres which shortened. Note that, it is normal for people in the study to have lost from 2 to 5% in their telomere length at their given ages during the course of the study, if left untreated.

A pattern has emerged among 4 of the 5 people whose baseline scores started well below the mean. Each score went up slightly in year 1, and then skyrocketed in year 2. This finding may reflect a delayed response to telomere length repair in people with poorer telomere health. While another commercial product (see U.S. Pat. No. 7,846,904, issued Dec. 7, 2010) proposes to lengthen telomeres by augmenting telomerase, without repairing DNA damage, this approach is questionable since increasing a cell's capacity to divide without decreasing DNA damage would be expected to increase the chances of accumulating cell mutations and epigenetic changes, which could lead to cancer. Without adequate repair, cells would replicate with an increased accumulation of damaged DNA, which can have a negative impact on health, aging, and disease. The biological effects of AC-11® address this issue in that it both lengthens telomeres and cellular life span while at the same time improving the natural DNA repair process.

The highest scoring patient went from an average telomere length to the $91^{st}$ percentile in year 1, and then tapered to 92% in year 2.

In order to ensure compliance, AC-11® was delivered to each patient on a monthly basis. The selected sample was a fairly homogenous sample: older, wellness oriented individuals with no known disease, ethical, and they paid for their own telomere testing. AC-11® was provided free of charge to each individual.

Whole blood was drawn from each subject, at appropriate timepoints, processed, and analyzed by SpectraCell, thereby providing unbiased data collection. Nucleated white blood cells were separated from whole blood and used to measure telomere length. Genomic DNA was isolated from the white blood cells and telomere length was evaluated according to the qPCR method of Cawthon, R M (2002, supra). The results were surprising and unexpected. Although the statistical sample is small, a clear and strong trend emerged in year one and continued into year two (see Table 1). Changes in telomere length is normally a very slow process, and is normally a shortening process (see standard curve in FIGS. 1-11).

Table 1. Telomere lengths for each subject before oral dosing and after one year and two years of 700 mg/day oral administration of an aqueous extract of *Uncaria tomentosa*. Subjects RC and MM stopped using AC-11®, for 4 to 5 months, in accordance with their doctor's request. Abbreviations: kb=kilobases.

| Subject | Baseline (kb) | Year 1 (kb) | Year 2 (kb) | Change (kb) |
|---|---|---|---|---|
| HV | 5.68 | 6.09 | 7.24 | +1.56 |
| EL | 4.57 | 4.57 | 5.52 | +0.95 |
| DB | 7.71 | 8.16 | 8.48 | +0.77 |
| LC | 6.4 | 7.98 | 8.06 | +1.66 |
| RC | 6.02 | 6.55 | 6.36 | +0.34 |
| LM | 5.15 | 5.37 | 7.44 | +2.29 |
| KC | 6.01 | 7.06 | 7.63 | +1.62 |
| BD | 5.67 | 6.62 | 7.74 | +2.07 |
| MM | 6.89 | 6.62 | 7.11 | +0.22 |
| JM | 7.27 | 7.7 | 7.67 | +0.40 |
| LCR | 5.2 | 5.45 | 6.8 | +1.60 |

Example 2

Toxicity Studies

Oral AC-11®, administered to rats in doses of 40, 80, or 160 mg/kg/day for up to 8 weeks did not result in any significant changes in food consumption or weight gain. Single oral doses up to 8 g/kg did not result in deaths or signs of acute toxicity. Thus, an $LD_{50}>8$ g/kg in rats has been reported (Sheng et al. (2000) J. Ethnopharm. 69: 115-26). Rats given 5 to 160 mg/kg of oral AC-11® showed no significant differences in liver, kidney, and spleen weights. One study did note that rats that were administered 80 mg/kg of AC-11® plus doxorubicin had a significantly increased mean heart weight coefficient (4.4%) when compared to animals that only received doxorubicin (0.386%±0.034 vs. 0.369%±0.022). However, there was no significant difference in mean heart weight when AC-11® plus doxorubicin treated animals were compared to untreated controls. Histopathological examination of tissues obtained from rats treated with 5 to 160 mg/kg/day of AC-11® for up to 8 weeks did not reveal an increase in pathological changes.

We claim:

1. A method of increasing lengths of telomeres in cells of a subject comprising:
   a) measuring lengths of one or more telomeres of a cell sample from the subject;
   b) administering to the subject an aqueous extract of an *Uncaria* species in a pharmaceutically effective amount and for a period of time sufficient to increase the lengths of said telomeres in said cells of said subject;
   c) re-measuring lengths of one or more telomeres, wherein if the telomeres have not lengthened, administering is continued; and
   d) said method resulting in lengthening of said telomeres.

2. The method of claim 1, wherein said aqueous extract is administered orally.

3. The method of claim 2, wherein the amount of said aqueous extract ranges from about 200 mg/day to about 700 mg/day, and further wherein said aqueous extract comprises a minimum of 8% weight/weight (w/w) carboxy alkyl esters (CAEs).

4. The method of claim 3, wherein the amount of said aqueous extract is about 700 mg/day.

5. The method of claim 4, wherein the subject is a human.

6. The method of claim 1, wherein said aqueous extract is formulated into a delivery means selected from the group consisting of a capsule, a tablet, a liquid, a syrup, and a gel.

7. The method of claim 1, wherein said aqueous extract is formulated into a transdermal patch.

8. The method of claim 2, wherein said aqueous extract is formulated into a delivery means selected from the group consisting of a capsule, a tablet, a liquid, a syrup, and a gel.

9. The method of claim 5, wherein said *Uncaria* species is *Uncaria tomentosa*.

10. The method of claim 1, wherein said subject is a human.

11. The method of claim 1, wherein said *Uncaria* species is *Uncaria tomentosa*.

12. The method of claim 1, wherein said period of time sufficient to increase the lengths of said telomeres in cells of said subject is at least 6 months.

13. The method of claim 1, wherein said period of time sufficient to increase the lengths of said telomeres in cells of said subject is at least 1 year.

14. The method of claim 7, wherein the transdermal patch delivers said extract to the subject over an extended period of time.

15. A method of increasing lengths of telomeres in cells of a subject comprising:
   (a) obtaining a sample of nucleated cells from a subject;
   (b) measuring lengths of telomeres in said sample of nucleated cells;
   (c) orally administering to said subject a daily dose of an effective amount of an aqueous extract of an *Uncaria* species for a period of time sufficient to increase the lengths of telomeres in cells of said subject;
   (d) obtaining a sample of nucleated cells from said subject after said period of time has been completed; and
   (e) measuring the lengths of telomeres in said sample of nucleated cells from said subject after said period of time has been completed;
   (f) comparing said lengths of said telomeres before said period of time has commenced with said lengths of said telomeres after said period of time has been completed; and (g) wherein if the telomeres have not lengthened, administering is continued.

16. The method of claim 15, wherein said period of time sufficient to increase the lengths of telomeres in a cell of said subject is at least one year.

17. The method of claim 15, wherein said nucleated cells are white blood cells.

18. The method of claim 15, wherein said subject is a human.

19. The method of claim 15, wherein said measuring steps (b) and (e) are carried out by quantitative polymerase chain reaction.

20. The method of claim 15, wherein said *Uncaria* species is *Uncaria tomentosa*.

* * * * *